US00PP13728P39

(12) United States Plant Patent
Scheffers

(10) Patent No.: US PP13,728 P3
(45) Date of Patent: Apr. 15, 2003

(54) DRACAENA PLANT NAMED '0101WS'

(76) Inventor: Ruud A. M. Scheffers, Plaats 9, 2675 CK, Honselersdijk (NL)

( * ) Notice: Subject to any disclaimer, the term of this patent is extended or adjusted under 35 U.S.C. 154(b) by 0 days.

(21) Appl. No.: 09/962,329

(22) Filed: Sep. 26, 2001

(65) Prior Publication Data

US 2002/0120971 P1 Aug. 29, 2002

(30) Foreign Application Priority Data

Feb. 26, 2001 (EP) ..... 2001/0355

(51) Int. Cl.[7] ..... A01H 5/00
(52) U.S. Cl. ..... Plt./383

(58) Field of Search ..... Plt./383

*Primary Examiner*—Bruce R. Campell
*Assistant Examiner*—Susan B. McCormick
(74) *Attorney, Agent, or Firm*—Foley & Lardner

(57) ABSTRACT

A distinct Dracaena plant named '0101WS' characterized by the three main colors in the leaves: the approximately 5 cm wide center is a collection of broad to very fine green and grayish green stripes; main colors include gray, RHS 188A, green RHS 139 A, and light gray, RHS 189 D; secondary colors in the center include small stripes of green, RHS 144 A and green varieties between RHS 139 A and 188 A; the center stripe is white, RHS 155 B, and approximately up to 12 mm wide; the outer stripe is green, RHS 144 A and approximately up to 5 mm wide; strong, leathery, lightly ribbed leaves; and leaf length 25 cm, leaf width 5–5.5 cm.

2 Drawing Sheets

LATIN NAME OF THE GENUS AND SPECIES OF THE PLANT CLAIMED

*Dracaena Vand. Ex. L. fragrans* (group Compacta)

VARIETY DENOMINATION

'0101WS'

BACKGROUND OF THE INVENTION

The present invention comprises a new and distinct cultivar of Dracaena plant botanically known as *Dracaena Vand. Ex. L. fragrans* (group Compacta) and hereinafter referred to the cultivar name '0101WS '.

The new cultivar was selected by the inventor, Ruud A. M. Scheffers, in Honselersdijk, in 1998. The new cultivar was obtained as a natural mutation of *Dracaena Vand. Ex. L. fragrans* (group Compacta) named 'Surprise' (unpatented).

The new cultivar was first asexually propagated by the inventor in Honselersdijk, The Netherlands, in 1998. Subsequent asexual reproduction of the new cultivar by division has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and in combination distinguish '0101WS' as a new and distinct cultivar:

1. three main colors in the length of the leaves: dark green (RHS 139 A), and grayish green center colors (RHS 188A and RHS 189D), secondary colors include: small green center stripes (RHS 144 A), and green varieties (between 139A and 188A), followed by a first rim of white (RHS 155B) and an outer rim of lemon color (RHS 144A);
2. strong, leathery, lightly ribbed leaves; and
3. leaf length 25 cm, leaf width 5–5.5 cm.

'0101WS' has not been observed under all possible environmental conditions. The phenotype on the new cultivar may vary significantly with variations in environment such as temperature, light intensity, and day length without any change in genotype. The following observations, measurements and values describe plants grown in Honselersdijk, The Netherlands under greenhouse conditions which closely approximate those generally used in horticultural practice.

In comparison with the well-known *Dracaena Vand. Ex. L. fragrans* (group Compacta) named 'Surprise', '0101WS' has three main colors in the length of the leaves: dark green center color, followed by a first, broad rim of white and an outer rim of lemon color. 'Surprise' does not have the broad white rim.

BRIEF DESCRIPTION OF THE DRAWINGS

The first drawing illustrates a 16 week old plant of Dracaena '0101WS' with colors being as true as possible with illustrations of this type. The second drawing illustrates a 16-weeks old plant of '0101WS' propagated from a top together with a 16-week old plant of 'Surprise' propagated from a tip.

DETAILED BOTANICAL DESCRIPTION

Color references are made to The Royal Horticultural Society Colour Chart (R.H.S.), except where general colors of ordinary significance are used. Colors are approximate as color depends on horticultural practices such as light level and fertilization rate, among others.

Parentage: *Dracaena Vand. Ex. L. fragrans* (group Compacta) 'Surprise'

Propagation: Primarily by vegetative division of the plant head or apical meristem.

General observations:

*Growing conditions.*—'0101WS' is grown in a greenhouse. The grower propagates '0101WS' in a nursery in a commercial greenhouse under 20–21 degrees Celsius temperatures day and night. As with most Dracaena varieties, '0101WS' does not stand direct sunlight so sun shields are closed when sunlight becomes too bright. No artificial lighting or photoperiodic treatments are conducted. Highest temperature resistance is at least 40 degrees Celsius, lowest is 5 degrees Celsius. Resistance, tolerance, and susceptibility to stresses, pathogens, and pests is very good. Compound fertilizer is added to the soil. There are no other cultural or environmental treatments.

Plant habit:

*Growth rate.*—Fast, mature plant growth approximately 20 weeks from the planting of a rooted cutting.

*Form.*—Compact.

*Plant height.*—17–19 cm in a 17 cm pot (16 week old plant).

*Plant width.*—35 cm in a 17 cm pot (16 week old plant).

Leaves:

*Form and size.*—Ensiform with acuminate tip, cuneate base.

*Texture.*—Strong and leathery, lightly ribbed.

*Leaf arrangement.*—Spiral.

*Length.*—25 cm.

*Width.*—Approximately 5 cm to 5.5 cm.

*Veins.*—One main vein, visible only on the underside of the leaf (mid-rib), RHS 137 B.

*Upper side color.*—Three main colors: the approximately 5 cm wide center is a collection of broad to very fine green and grayish green stripes. Colors include gray, RHS 188A; green, RHS 139 A; and light gray, RHS 189 D. Secondary colors in the center include small green stripes, RHS 144 A and green to grayish green varieties between RHS 139 A and 188 A. The outer stripe is green, RHS 144 A and approximately up to 5 mm wide.

*Under side color.*—Largely similar to upper side but less glossy and slightly lighter.

*Margin.*—Entire, lightly curled and thinner than center of leaf.

*Number.*—Approximately 18 leaves per plant when grown in a 17 cm pot for 16 weeks in the Netherlands.

Flowers: No flowers observed, this species only flowers when growing conditions are very poor.

Stem:

*Length.*—Approximately 3 cm.

*Diameter.*—1.5 cm and formed by bases of leaves.

*Color.*—Pure white.

Roots: Orange-brown, RHS 168 D; it takes approximately 3 weeks to initiate roots and approximately 7 weeks to produce a rooted liner.

Plant disease insect tolerance: '0101WS' has a very high resistance against diseases and a very high tolerance against insects.

Reproductive organs: No flowers observed, this species only flowers when growing conditions are very poor.

I claim:

1. A new and distinct cultivar of Dracaena plant named '0101WS', as described and illustrated herein.

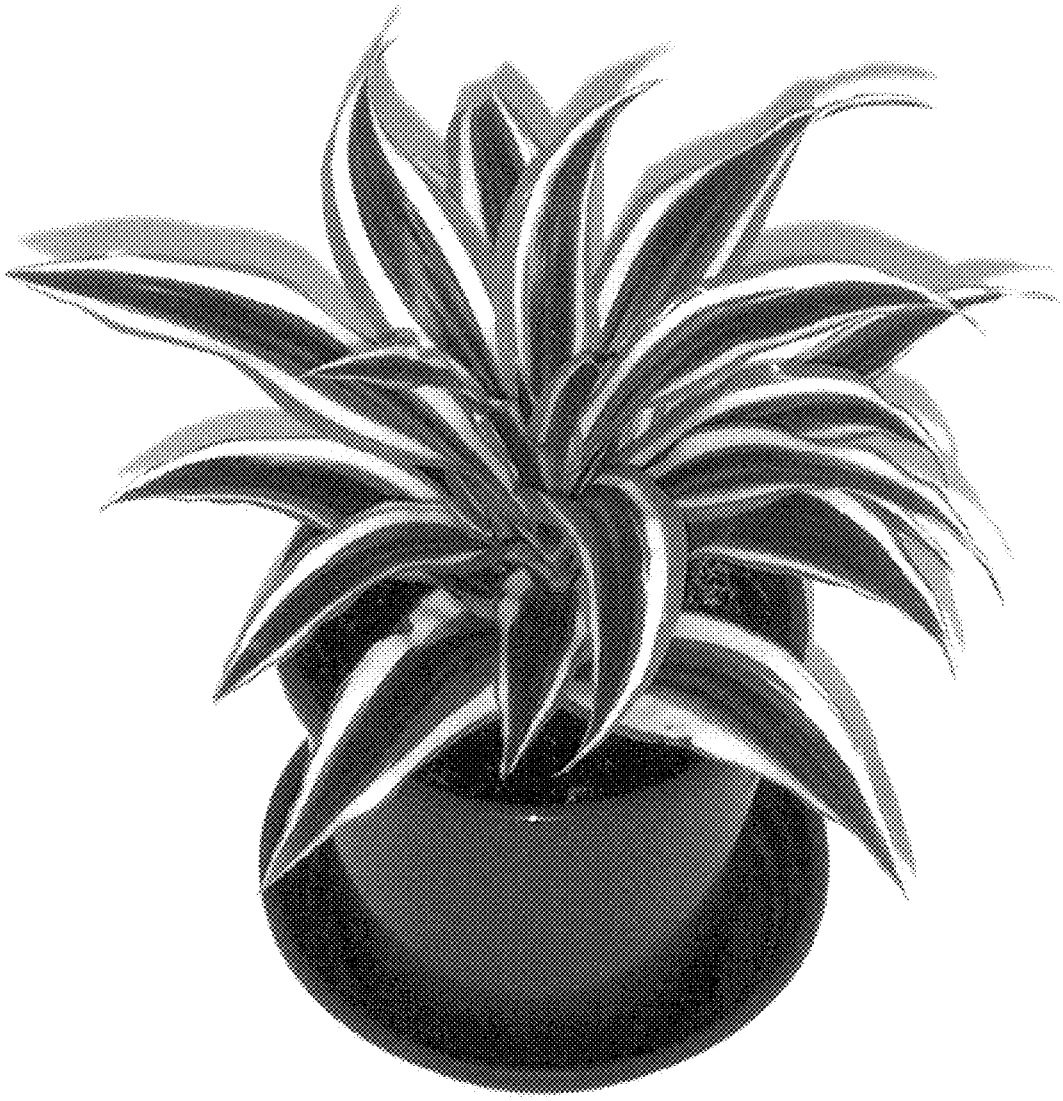

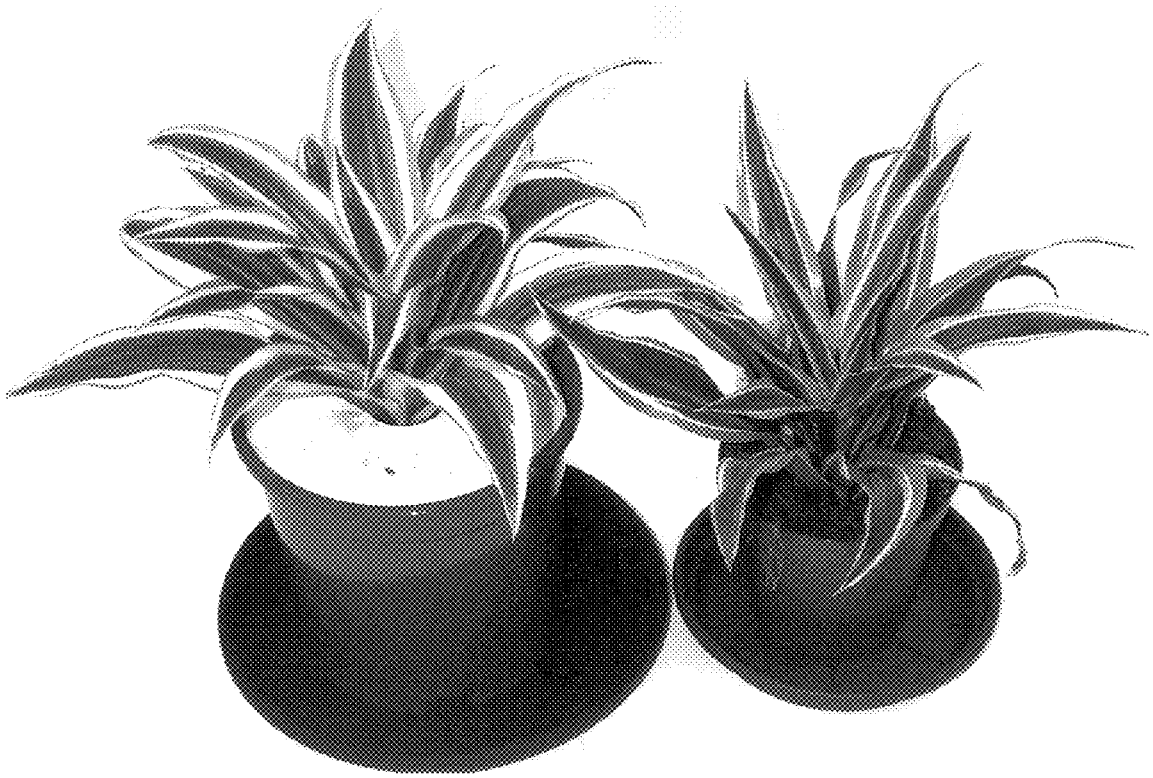

* * * * *